US010053460B2

United States Patent
Liu et al.

(10) Patent No.: US 10,053,460 B2
(45) Date of Patent: Aug. 21, 2018

(54) PROCESS FOR THE PREPARATION OF TERT-BUTYL 4-((2S,5R)-6-(BENZYLOXY)-7-OXO-1,6-DIAZABICYCLO[3.2.1]OCTANE-2-CARBOXAMIDO)PIPERIDINE-1-CARBOXYLATE AND ANALOGS THEREOF

(71) Applicant: Merck Sharp & Dohme Corp., Rahway, NJ (US)

(72) Inventors: Zhijian Liu, Kendall Park, NJ (US); Nobuyoshi Yasuda, Mountainside, NJ (US); Lu Yang, San Diego, CA (US); Artis Klapars, Edison, NJ (US); Kevin R. Campos, Berkeley Heights, NJ (US); Mikhail Reibarkh, Cranford, NJ (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 0 days.

(21) Appl. No.: 15/532,788

(22) PCT Filed: Nov. 30, 2015

(86) PCT No.: PCT/US2015/062884
§ 371 (c)(1),
(2) Date: Jun. 2, 2017

(87) PCT Pub. No.: WO2016/089718
PCT Pub. Date: Jun. 9, 2016

(65) Prior Publication Data
US 2017/0362233 A1    Dec. 21, 2017

Related U.S. Application Data

(60) Provisional application No. 62/086,420, filed on Dec. 2, 2014.

(51) Int. Cl.
C07D 471/08    (2006.01)
C07F 7/02    (2006.01)
C07F 7/10    (2006.01)
C07F 7/18    (2006.01)

(52) U.S. Cl.
CPC .............. *C07D 471/08* (2013.01); *C07F 7/10* (2013.01); *C07F 7/1868* (2013.01)

(58) Field of Classification Search
CPC ................................ C07D 471/08; C07F 7/02
USPC .................................... 546/121, 14; 556/408
See application file for complete search history.

(56) References Cited

U.S. PATENT DOCUMENTS

| 6,172,250 | B1 | 1/2001 | Seguin |
| 6,211,393 | B1 | 4/2001 | Seguin |
| 7,112,592 | B2 | 9/2006 | Lampilas et al. |
| 8,487,093 | B2 | 7/2013 | Blizzard et al. |
| 2003/0199541 | A1 | 10/2003 | Lampilas et al. |
| 2014/0163230 | A1* | 6/2014 | Ronsheim ............ C07D 211/60 546/121 |
| 2014/0303375 | A1 | 10/2014 | Abe |

FOREIGN PATENT DOCUMENTS

| WO | WO200210172 | 2/2002 |
| WO | WO2008039420 | 4/2008 |
| WO | WO20100126820 | 11/2010 |
| WO | WO2012172368 | 12/2012 |
| WO | WO2014200786 | 12/2014 |

OTHER PUBLICATIONS

Baldwin, Jack E. et al., A Novel Entry to Carbenoid Species via Beta-Ketosulfoxonium Ylides, J. Chem. Soc. Chem. Commun., 1993, 1434-1435, 18.
Mangion, Ian K. et al., A Concise Synthesis of a Beta-Lactamase Inhibitor, Org. Lett., 2011, 5480-5483, 13.
Mangion, Ian K. et al., Iridium-Catalyzed X-H Insertions of Sulfoxonium Ylides, Org. Lett., 2009, 3566-3569, 11.
Miller, Steven P. et al., Practical and Cost-Effective Manufacturing Route for the Synthesis of a Beta-Lactamase Inhibitor, Org. Lett, 2014, 174-177, 16.

* cited by examiner

*Primary Examiner* — Charanjit Aulakh
(74) *Attorney, Agent, or Firm* — Patricia A. Shatynski; John C. Todaro

(57) ABSTRACT

The present invention relates to processes for preparing compounds of Formula I. Such compounds include intermediates in the manufacture of 7-oxo-1,6-diazabicyclo[3.2.1]octane-2-carboxamide beta-lactamase inhibitors such as (2S,5R)-7-oxo-N-5 piperidin-4-yl-6-(sulfoxy)-1,6-diazabicyclo[3.2.1]octane-2-carboxamide. The present invention also relates to novel intermediates formed i these processes. The present invention relates to a process for preparing a compound of Formula I or a pharmaceutically acceptable salt thereof.

18 Claims, No Drawings

PROCESS FOR THE PREPARATION OF TERT-BUTYL 4-((2S,5R)-6-(BENZYLOXY)-7-OXO-1,6-DIAZABICYCLO[3.2.1]OCTANE-2-CARBOXAMIDO)PIPERIDINE-1-CARBOXYLATE AND ANALOGS THEREOF

FIELD OF THE INVENTION

The invention is related to the preparation of (2S,5R)-6-(benzyloxy)-7-oxo-1,6-diazabicyclo[3.2.1]octane-2-carboxamides and analogs thereof. These carboxamides are suitable for use as intermediates that lead via a series of additional process steps to the preparation of the beta lactamase inhibitors, including (2S,5R)-7-oxo-N-piperidin-4-yl-6-(sulfoxy)-1,6-diazabicyclo[3.2.1]octane-2-carboxamide.

BACKGROUND OF THE INVENTION

Certain 7-oxo-1,6-diazabicyclo[3.2.1]octane-2-carboxamides are inhibitors of β-lactamase and, when used in conjunction with β-lactam antibiotics, can be effective for the treatment of bacterial infections. See, for example, U.S. Pat. No. 8,487,093 which discloses 7-oxo-1,6-diazabicyclo[3.2.1]octane-2-carboxamides and their synthesis from a ketosulfoxonium ylide intermediate containing an amide side chain, where the ylide intermediate is cyclized to a 5-oxo-piperidine-2-carboxamide using an Ir, Rh, or Ru catalyst. Similarly, Baldwin et al. disclose the transformation of lactone-derived β-ketosulfoxonium ylides into β-oxonitrogen heterocycles in the presence of a rhodium catalyst. See Baldwin et al., 1993, *J. Chem. Soc., Chem. Commun.* 18:1434-1435. Mangion et al. disclose iridium-catalyzed X-H insertions (e.g., N—H insertions) of sulfoxonium ylides. See Mangion et al., 2009, *Org. Lett.*, 11:3566-3569 and Mangion et al., 2011, *Org. Lett.* 13:5480-5483.

U.S. Pat. No. 7,112,592 discloses heterocyclic compounds and their salts, processes for making the compounds and methods of using the compounds as antibacterial agents. One such compound is sodium salt of 7-oxo-6-(sulphoxy)-1,6-diazabicyclo[3.2.1]octane-2-carboxamide. U.S. Patent Application Publication No. US2003/0199541 discloses methods for preparing azabicyclic compounds which are useful as medicaments, in particular anti-bacterial agents. International Patent Application Publication Nos. WO 2002/10172, WO2008/039420 and WO2012/172368 disclose methods for preparing certain 7-oxo-1,6-diazabicyclo[3.2.0]heptane-2-carboxamides or trans-7-oxo-6-(sulphoxy)-1,6-diazabicyclo[3.2.1]octane-2-carboxamides which are useful as β-lactamase inhibitors.

International Patent Application Publication No. WO2010/126820 discloses the preparation of alkyl esters of N-protected oxo-azacycloalkylcarboxylic acids. These esters can be used as intermediates in the synthesis of 7-oxo-1,6-diazabicyclo[3.2.1]octane-2-carboxamides and esters.

SUMMARY OF THE INVENTION

The present invention relates to a process for preparing a compound of Formula I:

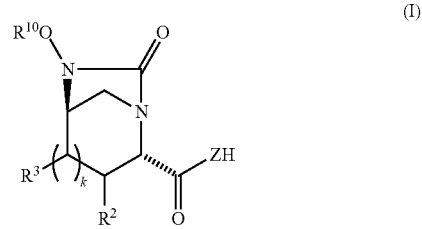

or a pharmaceutically acceptable salt thereof; comprising:
(a) reacting a compound of Formula (II):

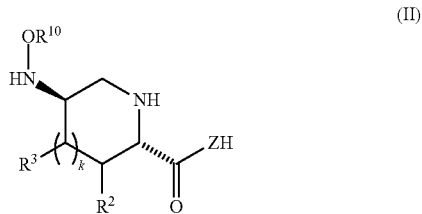

with a compound of formula (X)

and a base to obtain a compound of Formula (III) or (IV), or a mixture thereof;

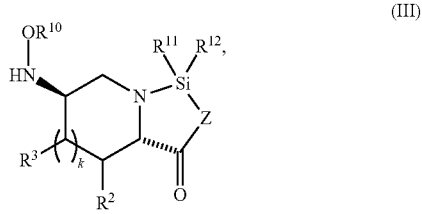

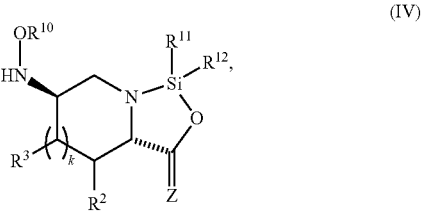

(b) treating the compound of formula (III) or (IV), or a mixture thereof, with phosgene or a phosgene equivalent to obtain a compound of formula (V) or (VI), or a mixture thereof,

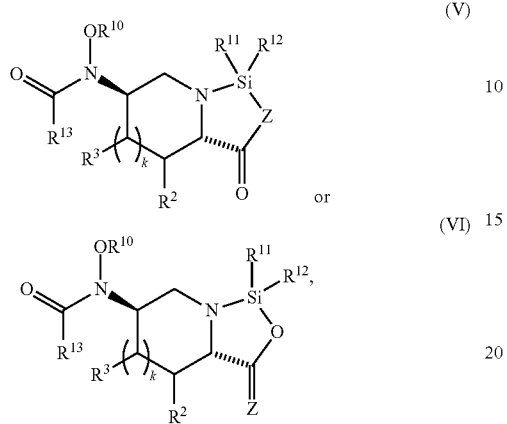

and (c) treating the compound of formula (V) or (VI), or the mixture thereof, with a hydrolysis reagent to obtain the compound of formula (I); wherein Z is O or —NR$^5$;

k is an integer equal to 0, 1, or 2;

R$^2$ and R$^3$ are defined as follows:

(a) R$^2$ is H, C$_{1-6}$ alkyl, —O—C$_{1-6}$ alkyl, —O—Si—(C$_{1-6}$ alkyl)$_3$, or —O—Si—(C$_{1-6}$ alkyl)(phenyl)$_2$, and each R$^3$ is H or C$_{1-6}$ alkyl; or (b) alternatively and with the proviso that k is 1 or 2, R$^2$ and the R$^3$ adjacent to R$^2$ together with the carbon atoms to which each is attached form C$_{5-7}$ cycloalkyl which is optionally substituted with from 1 to 3 substituents each of which is independently C$_{1-6}$ alkyl, —O—C$_{1-6}$ alkyl, —O—Si—(C$_{1-6}$ alkyl)$_3$, or —O—Si—(C$_{1-6}$ alkyl)(phenyl)$_2$; and any other R$^3$ is H or C$_{1-6}$ alkyl;

R$^5$ is H, C$_{1-6}$ alkyl, C$_{3-6}$ cycloalkyl, aryl, C$_{1-6}$ alkyl-aryl, heteroaryl, C$_{i-6}$ alkyl-heteroaryl, or

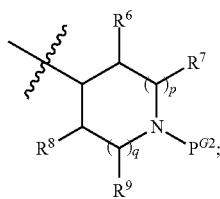

R$^6$ and R$^8$ are independently H, C$_{1-3}$ alkyl, —O—C$_{1-3}$ alkyl, or —N—(C$_{1-3}$ alkyl)$_2$; each R$^7$ and R$^9$ is independently H or C$_{1-6}$ alkyl;

P$^{G2}$ is an amine protecting group selected from carbamates, benzylamines, sulfonamides and amides;

R$^{10}$ is benzyl or allyl, wherein the benzyl or ally is optionally substituted with C$_{1-6}$ alkyl, C$_{1-6}$ alkoxy, fluoro, or —NO$_2$;

R$^{11}$ and R$^{12}$ are C$_{1-6}$ alkyl or aryl; or

R$^{11}$ and R$^{12}$ together with the silane to which they are attached form a 4-to 6-membered saturated monocyclic ring containing 0 or 1 heteroatoms selected from N and O which is optionally fused with 1 or 2 aromatic rings each optionally containing 0 or 1 heteroatoms selected from N and O;

R$^{13}$ is a leaving group;

p is 0, 1, or 2;

q is 0, 1, or 2;

p+q=0, 1, 2, or 3; and

R$^a$ and R$^b$ are halo.

In one embodiment of the invention, Z is —NR$^5$. In one embodiment of the invention, k is 1. In one embodiment of the invention, R$^2$ and R$^3$ are H. In one embodiment of the invention, R$^5$ is H or

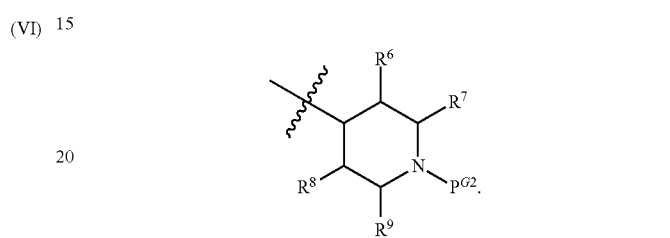

In one aspect of this embodiment, R$^5$ is

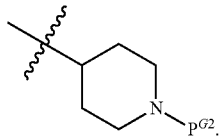

In one embodiment of the invention, p$^{G2}$ is t-Boc.

In step (a) of invention, in one embodiment, the compound of Formula X is a dihalodialkylsilane, dihalodiarylsilane, or dihaloalkylarylsilane. In one aspect of the embodiment, the compound of Formula X is dichlorodimethylsilane. In one embodiment, the base is Hunig's base.

In step (b) of the invention, in one embodiment, the phosgene equivalent is carbonyldiimidazole.

In step (c) of the invention, in one embodiment, the hydrolysis reagent is a protic solvent, acid or fluoride source. In one aspect of this embodiment, the hydrolysis reagent is a protic solvent, which can be isopropyl alcohol.

In certain embodiments of the invention, the compound of Formula (I) is tert-butyl 4-((2S,5R)-7-oxo-6-benzyloxy-1,6-diazabicyclo[3.2.1]octane-2-carboxamido)piperidine-1-carboxylate or a pharmaceutically acceptable salt thereof.

The present invention also relates to a compound which is:

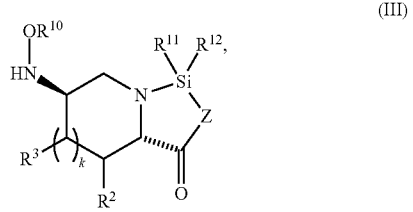

-continued

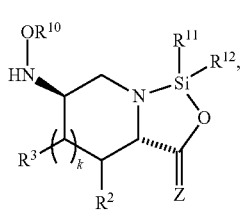
(IV)

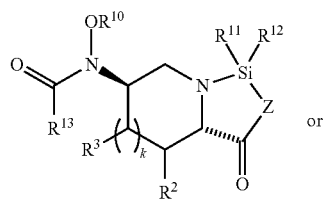
(V)

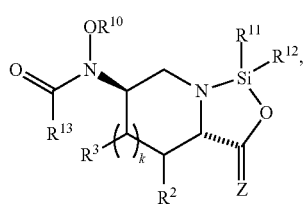
(VI)

or a salt thereof wherein
Z is O or —NR$^5$;
k is an integer equal to 0, 1, or 2;
R$^2$ and R$^3$ are defined as follows:
(a) R$^2$ is H, C$_{1-6}$ alkyl, —O—C$_{1-6}$ alkyl, —O—Si—(C$_{1-6}$ alkyl)$_3$, or —O—Si—(C$_{1-6}$ alkyl)(phenyl)$_2$, and each R$^3$ is H or C$_{1-6}$ alkyl; or
(b) alternatively and with the proviso that k is 1 or 2, R$^2$ and the R$^3$ adjacent to R$^2$ together with the carbon atoms to which each is attached form C$_{5-7}$ cycloalkyl which is optionally substituted with from 1 to 3 substituents each of which is independently C$_{1-6}$ alkyl, —O—C$_{1-6}$ alkyl, —O—Si—(C$_{1-6}$ alkyl)$_3$, or —O—Si—(C$_{1-6}$ alkyl)(phenyl)$_2$; and any other R$^3$ is H or C$_{1-6}$ alkyl;
R$^5$ is H, C$_{1-6}$ alkyl, C$_{3-6}$ cycloalkyl, aryl, C$_{1-6}$ alkyl-aryl, heteroaryl, C$_{1-6}$ alkyl-heteroaryl, or

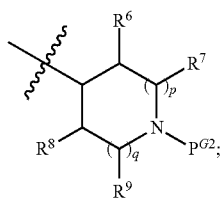

R$^6$ and R$^8$ are independently H, C$_{1-3}$ alkyl, —O—C$_{1-3}$ alkyl, or —N—(C$_{1-3}$ alkyl)$_2$; each R$^7$ and R$^9$ is independently H or C$_{1-6}$ alkyl;
P$^{G2}$ is an amine protecting group selected from carbamates, benzylamines, sulfonamides, and amides;
R$^{10}$ is benzyl or allyl, wherein the benzyl or allyl is optionally substituted with C$_{1-6}$ alkyl, C$_{1-6}$ alkoxy, fluoro, or —NO$_2$;
R$^{11}$ and R$^{12}$ are C$_{1-6}$ alkyl or aryl; or
R$^{11}$ and R$^{12}$ together with the silane to which they are attached form a 4-to 6-membered saturated monocyclic ring containing 0 or 1 heteroatoms selected from N and O which is optionally fused with 1 or 2 aromatic rings each optionally containing 0 or 1 heteroatoms selected from N and O;
R$^{13}$ is a leaving group;
p is 0, 1, or 2;
q is 0, 1, or 2;
p+q=0, 1, 2, or 3.

In certain embodiments, Z is —NR$^5$. In certain aspects of the invention, the compound is a compound which is:

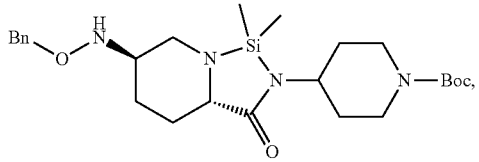

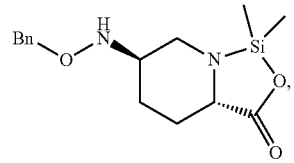

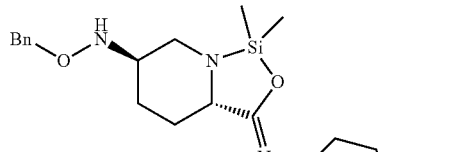

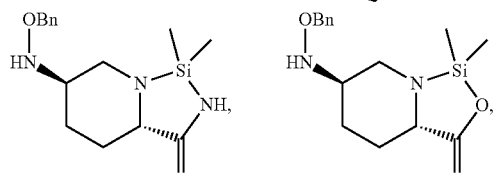

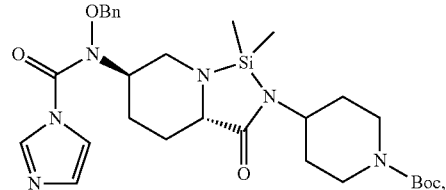

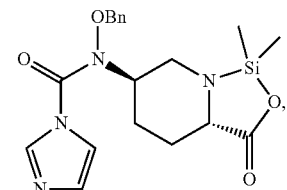

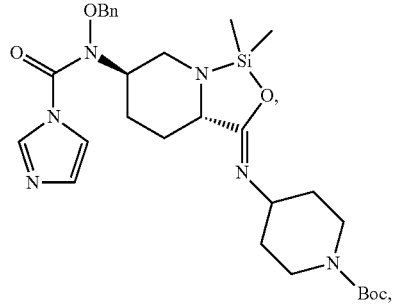

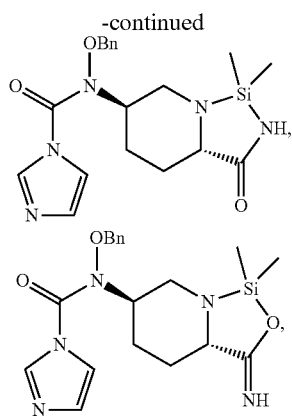

or a salt thereof.

Other embodiments, aspects and features of the present invention are either further described in or will be apparent from the ensuing description, examples, and appended claims.

DETAILED DESCRIPTION OF THE INVENTION

The present invention relates to a process for preparing a compound of Formula I, a urea intermediate in the synthesis of 7-oxo-1,6-diazabicyclo[3.2.1]octane-2-carboxamides, and pharmaceutically acceptable salts thereof, employing a silicon-containing compound in conjunction with phosgene or a phosgene equivalent such as carbonyldiimidazole (CDI). The silicon-containing compound can react with the diamine of Formula II in the presence of a base, such as Hunig's base, to generate a novel 5-membered N—Si—N (III) or N—Si—O (IV) intermediate in the case where Z is —NR$^5$, followed by reaction with phosgene or a phosgene equivalent (e.g., CDI) to generate a compound of Formula V or VI, or a mixture thereof The desired urea can then be formed through hydrolysis of the silyl group with water, an alcohol, or fluoride ion and spontaneous cyclization. Partial silylation at the nitrogen in the hydroxylamine moiety in the compounds of Formula III and/or IV was observed at the first silylation stage, but upon the reaction with CDI the partially silylated intermediates were cleanly converted to the compound of Formula V or VI, or a mixture thereof High quality urea is isolated in around 90% yield after standard work up. A compound of Formula I is useful as an intermediate in the process for the synthesis of the beta-lactamase inhibitor, (2S,5R)-7-oxo-N-piperidin-4-yl-6-(sulfoxy)-1,6-diazabicyclo[3.2.1]octane-2-carboxamide.

Moreover the isolated material gives superior performance in the subsequent synthetic step—a palladium catalyzed de-benzylation.

The original process for preparation of the urea of Formula I involved treating the diamine of Formula II with triphosgene. Early attempts to replace triphosgene with CDI, a greener and safer reagent compared with triphosgene, did not provide a satisfactory yield of the desired urea due to competing reactions of the other nitrogen atoms in the molecule. The inventors of the present invention have discovered that through the use of a silicon-containing compound yields of the desired urea intermediate can be improved.

As such, the present invention provides a safer, highly selective, more robust and greener process for the cyclic urea formation which utilizes a silicon-containing compound such as dichlorodimethysilane to introduce a temporary protecting group, in combination with phosgene or a phosgene equivalent, such as CDI, as a carbonylation reagent.

The term "alkyl" refers to a monovalent straight or branched chain, saturated aliphatic hydrocarbon radical having a number of carbon atoms in the specified range. Thus, for example, "$C_{1-6}$ alkyl" (or "$C_1$-$C_6$ alkyl") refers to any of the hexyl and pentyl alkyl isomers as well as n-, iso-, sec- and t-butyl, n- and iso- propyl, ethyl and methyl. As another example, "$C_{1-4}$ alkyl" refers to any of n-, iso-, sec- and t-butyl, n- and isopropyl, ethyl and methyl. As another example, "$C_{1-3}$ alkyl" refers to any of n-propyl, isopropyl, ethyl and methyl.

The term "branched alkyl" refers to an alkyl group as defined above except that straight chain alkyl groups in the specified range are excluded. As defined herein, branched alkyl includes alkyl groups in which the alkyl is attached to the rest of the compound via a secondary or tertiary carbon; e.g., isopropyl is a branched alkyl group.

The term "allyl" refers to a substituent with the structural formula H$_2$C═CH—CH$_2$R, where R is a substituent. An allyl is optionally substituted at any carbon atom which $C_{1-4}$ alkyl or aryl.

The term "aryl" refers to an aromatic monocyclic or bicyclic ring system comprising from 5 to 14 carbon atoms, e.g., 5 to 8 carbon atoms. In certain embodiments, a monocyclic aryl will comprise from 5 to 7 carbon atoms. In certain embodiments, a bicyclic aryl will comprise from 8 to 11 carbon atoms. Suitable aryl groups include phenyl, naphthyl and anthracenyl. An aryl is optionally substituted with halogen, $C_{1-6}$ alkyl, —O—$C_{1-6}$ alkyl, —CN or —NO$_2$.

The term "halogen" (or "halo") refers to fluorine, chlorine, bromine or iodine (alternatively referred to as fluoro, chloro, bromo, or iodo). In certain embodiments of the invention, the halogen is chlorine or bromine. In one aspect of these embodiments, the halogen is chlorine.

The term "heteroaryl" refers to an aromatic monocyclic or bicyclic ring system containing 1 to 3 heteroatoms selected from N, S, and O and comprising from 5 to 14 carbon atoms, e.g., 5 to 8 carbon atoms. In certain embodiments, a monocyclic heteroaryl will comprise from 5 to 7 carbon atoms. In certain embodiments, a bicyclic heteroaryl will comprise from 8 to 11 carbon atoms. Suitable heteroaryl groups include, but are not limited to, pyrrolyl, imidazolyl, pyrazolyl, oxazolyl, isoxazolyl, thiazolyl, isothiazolyl, furanyl, pyridinyl, indolyl, quinolidinyl, benzoimidazolyl, benzoxazoyl, benzoisoxazolyl, and benzothiazolyl. A heteroaryl is optionally substituted with halogen, $C_{1-6}$alkyl, —OC$_{1-6}$alkyl, or —NO$_2$.

The term "leaving group" refers to a molecular fragment that departs with a pair of electrons in heterolytic bond cleavage. Leaving groups can be anions or neutral molecules, but in either case it is crucial that the leaving group be able to stabilize the additional electron density that results from bond heterolysis. Common anionic leaving groups are halides such as Cl$^-$, Br$^-$, and I$^-$, sulfonate esters, such as tosylate (TsO$^-$), triflate (TfO$^-$), mesylate (MsO$^-$), aryloxy groups, such as p-nitrophenyl, o-nitrophenyl, o,p-dinitrophenyl and pentafluorophenyl, and heterocycloxy groups, such as 2-methyl-2-pyridinyloxy, 2-oxo-2-pyridinyloxy, pyrrolidine-2,5 -dione-1-oxy, isoindoline-1,3 -dione-2-oxy, and 1H-benzo [d] [1.2.3]triazole-1-oxy. Suitable leaving groups include, but are not limited to halogen, imidazolyl, —O—$C_{1-6}$ alkyl, —O-aryl, and —O-heteroaryl.

The term "protic solvent" refers to any solvent that has a hydrogen atom bound to an oxygen (as in a hydroxyl group) or a nitrogen (as in an amine group). In general terms, any solvent that contains labile $H^+$ is called a protic solvent. The molecules of such solvents readily donate protons ($H^+$) to reagents. Protic solvents include, but are not limited to, formic acid, n-butanol, sec-butanol, tert-butanol, isopropanol, propanol, nitromethane, ethanol, methanol, acetic acid and water.

$P^{G2}$ is an amine protective group which, in combination with the amino nitrogen to which it is attached, is suitably an carbamate including alkyl carbamate, aryl carbamate, vinyl carbamate, allyl carbamate, benzylamine (optionally substituted), or amide including sulfonamide. Suitable $P^{G2}$ groups include 9-fluorenylmethoxycarbonyl (Fmoc), tert-butoxycarbonyl (Boc), benzyloxycarbonyl (Cbz), allyloxycarbonyl (Alloc), methoxybenzyl, nitrobenzyl, and benzyl. In some embodiments, $P^{G2}$ may be a protecting group and includes Fmoc, Boc, Cbz, ethyl- or methyloxycarbonyl, phenoxycarbonyl, Alloc and equivalent groups known to one skilled in the art with the benefit of this disclosure. In exemplary embodiments, $P^{G2}$ may be tert-butoxycarbonyl (Boc).

Unless expressly stated to the contrary, all ranges cited herein are inclusive; i.e., the range includes the values for the upper and lower limits of the range as well as all values in between. For example, a phenyl ring described as optionally substituted with "1 to 3 substituents" is intended to include as aspects thereof, a ring substituted with 0 to 3 substituents, 1 to 3 substituents, 2 to 3 substituents, 3 substituents, 1 to 2 substituents, 2 substituents, 1 substituent, and 0 substituents. As another example, temperature ranges, ranges of equivalents, and the like described herein include the upper and lower limits of the range and any value in the continuum there between.

Step (a) involves:
reacting a compound of Formula (II):

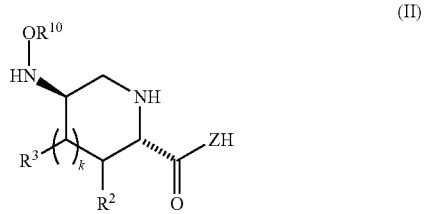

(II)

with a compound of formula (X)

(X)

and a base to obtain a compound of Formula (III) or (IV), or a mixture thereof;

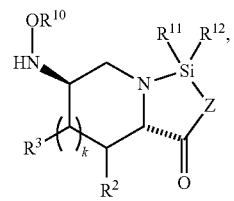

(III)

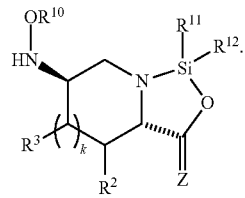

(IV)

Compounds of Formula II can be obtained as described in International Patent Application Publication No. WO2010/126820 and WO2012/172368, International Patent Application No. PCT/US14/040983, Mangion et al., 2009, *Org. Lett.*, 11:3566-3569, Mangion et al., 2011, *Org. Lett.* 13:5480-5483, and Miller et al., 2014, *Org. Lett.* 16:174.

In certain embodiments, Compound II includes the following:

(1a) k is 0 or 1;
(1b) k is 0;
(1c) k is 1;
(2a) $R^2$ is H, $C_{1-4}$ alkyl, —O—$C_{1-4}$ alkyl, —O—Si—$(C_{1-4}$ alkyl$)_3$, or —O—Si—$(C_{1-4}$ alkyl)(phenyl)$_2$, and each $R^3$ is H or $C_{1-4}$ alkyl;
(2b) $R^2$ is H, $CH_3$, —$OCH_3$, —O-trimethylsilyl (TMS), —O-t-butyldiphenylsilyl (TBDPS), —O-t-butyldimethylsilyl (TBS), or —O-triisopropylsilyl (TIPS), and each $R^3$ is H or $CH_3$;
(2c) $R^2$ is H or $CH_3$, and each $R^3$ is H or $CH_3$;
(2d) $R^2$ is H, and each $R^3$ is H;
(2e) with the proviso that k is 1 or 2, $R^2$ and the $R^3$ adjacent to $R^2$ together with the carbon atoms to which each is attached form $C_{5-6}$ cycloalkyl; and any other $R^3$ is H.

One or more of these embodiments (1) to (2) can be combined with each other, wherein each such combination is a separate embodiment. In other words, any embodiment from group 1 (1a, 1b, or 1c) can be combined with any embodiment from group 2 (2a, 2b, 2c, 2d or 2e).

In one embodiment of the invention, Z is —$NR^5$. In one embodiment of the invention, k is 1. In one embodiment of the invention, $R^2$ and $R^3$ are H. In one embodiment of the invention, $R^5$ is H or

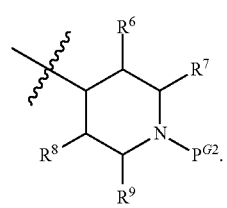

In one aspect of this embodiment, $R^5$ is

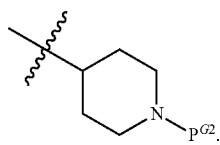

In one embodiment of the invention, $P^{G2}$ is t-Boc.

In specific embodiments, a compound of formula II is selected from

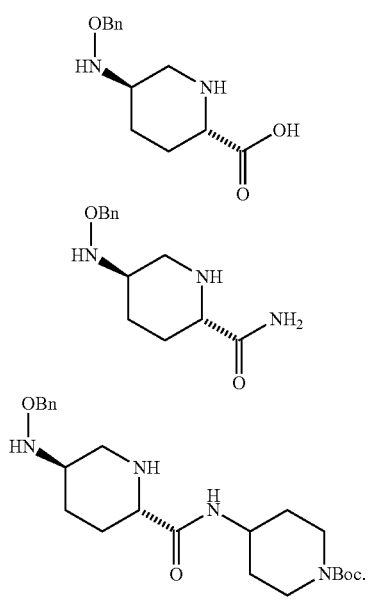

Compounds of formula X are silicon-containing compounds. In certain embodiments, $R^a$ and $R^b$ are independently selected from chloro or bromo. In one aspect of this embodiment, $R^a$ and $R^b$ are chloro. In certain embodiments, $R^{11}$ and $R^{12}$ are $C_{1-6}$ alkyl or aryl. In certain embodiments, $R^{11}$ and $R^{12}$ together with the silicon atom to which they are attached form a 4-to 6-membered saturated monocyclic ring containing 0 or 1 heteroatoms selected from N and O, which is optionally fused with 1 or 2 aromatic rings each optionally containing 0 or 1 heteroatoms selected from N, S, and O. In embodiments, where 2 aromatic rings are each fused to the saturated monocyclic ring, the aromatic rings can be separated or fused to each other.

Examples of suitable silicon-containing compounds include dichlorodimethylsilane dichloromethylethylsilane, dichlorodiethylsilane, dichloromethylisopropylsilane, dichloroethylisopropylsilane, dichlorodiisopropylsilane, dichloromethyl-tert-butylsilane, dichlorodiphenylsilane and compounds whose structures are set forth below.

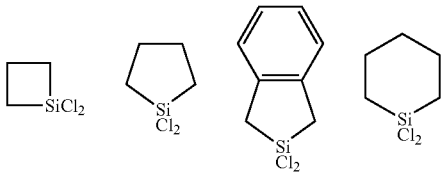

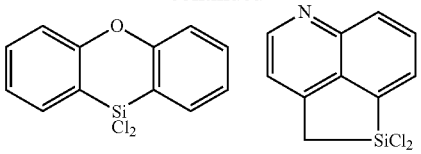

The silicon-containing compound is typically employed in an amount in a range of from about 0.5 to about 6 equivalents per equivalent of compound of Formula II, and is more typically employed in an amount in a range of from about 1 to about 2 equivalents (e.g., about 1.25 equivalents).

Suitable bases include organic bases and inorganic bases. Examples of suitable bases include, but are not limited to Hunig's base, triethylamine, N-methylmorpholine, pyridine, substituted pyridines, lutidine, and colidine. The base is typically employed in an amount in a range of from about 1 to about 6 equivalents per equivalent of the compound of Formula II, and is more typically employed in an amount in a range of from about 2.5 to about 5 equivalents (e.g., about 3.2 equivalents).

Step (a) is conducted in any suitable organic solvent, i.e., one in which the reactants are soluble. Suitable solvents include, but are not limited to, DCM and acetonitrile. A preferred solvent is acetonitrile.

The reacting of a compound of Formula II with a silicon-containing compound can suitably be conducted at a temperature in a range of from about −10° C. to about 40° C. and is typically conducted at a temperature in a range of from about −5° C. to about 20° C. (e.g., about 5° C.). Generally, a mixture of the compound of Formula III and the compound of Formula IV is generated. However, when Z is O, then the compounds of Formula III and IV are identical. At lower temperature, a greater proportion of the compound of Formula IV is present and at higher temperatures, a greater proportion of the compound of Formula III is present.

Step (b) involves treating the compound of Formula (III) or (IV) with phosgene or a phosgene equivalent to obtain a compound of Formula (V) or (VI), or a mixture thereof

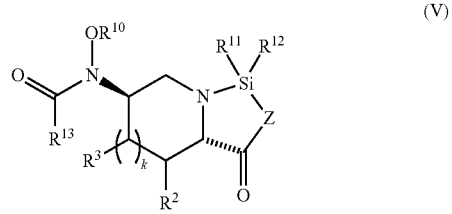

(V)

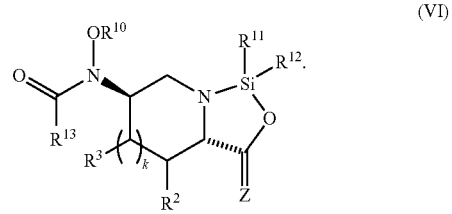

(VI)

The predominant species is the compound of Formula (V).

A suitable phosgene equivalent is one which provides a suitable source for a carbonylation reaction. Examples of phosgene equivalents include diphosgene, triphosgene, carbodiimidazole and haloformate, e.g., trichloromethylchloroformate.

Phosgene or a phosgene equivalent is typically employed in an amount in a range of from about 1 to about 4 equivalents per equivalent of Compound II, and is more typically employed in an amount in a range of from about 1 to about 2 equivalents (e.g., about 1.5 equivalents).

The contacting of compounds of Formula III and/or IV with phosgene or the phosgene equivalent can suitably be conducted at a temperature in a range of from about 15° C. to about 80° C. and is typically conducted at a temperature in a range of from about 35° C. to about 55° C.

Step (c) involves treating the compound of Formula (V) or (VI), or a mixture thereof, with a hydrolysis reagent to obtain the compound of formula (I). The hydrolysis reagent is any reagent which provides for selective hydrolysis of the Si—N bonds in the compounds of Formula (V) or (VI). Examples of hydrolysis reagents include protic solvents, water, acids such as hydrofluoric acid, phosphoric acid, toluenesulfonic acid and fluoride sources. Addition of water or a variety of alcohols (for example, primary alcohols such as MeOH, EtOH, n-PrOH, secondary alcohols such as IPA, and tertiary alcohols such as tert-BuOH) will hydrolyze the Si—N and/or Si—O bonds. In one embodiment, the hydrolysis reagent is IPA. The amount of IPA used has minimum impact for the reaction profile. The optimum amount of IPA is 2-6 equivalents (of the total of the compounds of Formula (V) and (VI)).

The compound of Formula I obtained through the processes of the invention can subsequently be processed as described in International Patent Application Nos. WO2010/126820 and WO2012/172368, International Patent Application No. PCT/US14/040983, Mangion et al., 2009, *Org. Lett.*, 11:3566-3569, Mangion et al., 2011, *Org. Lett.* 13:5480-5483 or and Miller et al., 2014, *Org. Lett.* 16:174 to obtain a beta lactamase inhibitor such as (2S,5R)-7-oxo-N-piperidin-4-yl-6-(sulfoxy)-1,6-diazabicyclo[3.2.1]octane-2-carboxamide.

The solvents, agents, catalysts, reaction amounts, reaction temperatures, etc. described above for Steps (a) to (c) leading to compound of Formula I are applicable to steps (a) to (c) set forth in the preceding sub-embodiment leading to compound 1, except where express limitations are placed upon one or more of these variables in the sub-embodiments.

In one particular embodiment, the present invention provides a process for preparing compound 1:

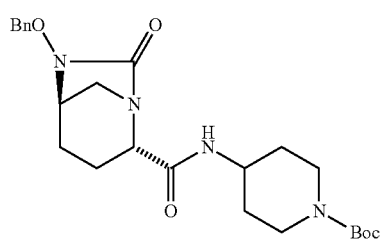

(1)

or a pharmaceutically acceptable salt thereof; comprising:

(a) treating a compound 2

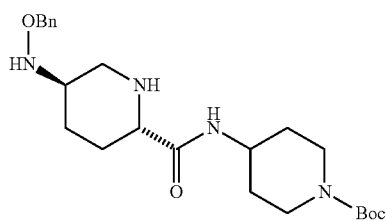

(2)

with dichlorodimethylsilane and Hunig's base in the presence of an organic solvent, such as acetonitrile, to obtain compound 3 or 4, or a mixture thereof,

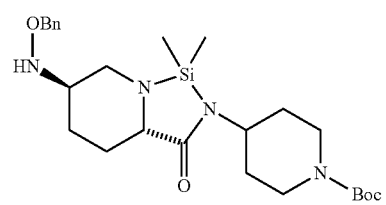

(3)

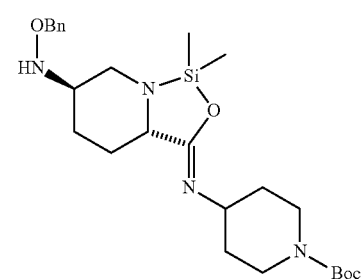

(4)

(b) treating compound 3 or 4, or the mixture thereof, with carbonyldiimidazole to obtain compound 5 or 6, or a mixture thereof; and

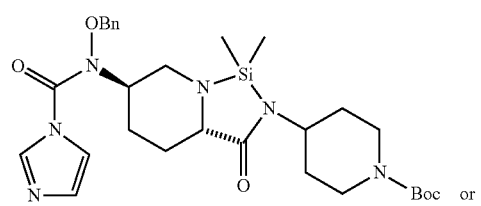

(5)

or

-continued

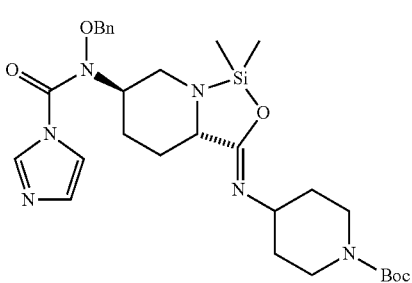

(6)

(c) treating compound 5 or 6, or the mixture thereof, with isopropyl alcohol to obtain compound 1.

Compounds such as (2S,5R)-7-oxo-N-piperidin-4-yl-6-(sulfoxy)-1,6-diazabicyclo[3.2.1]octane-2-carboxamide can exhibit inhibition of β-lactamase and thus can be used as β-lactamase inhibitors in combination with β-lactam antibiotics (e.g., imipenem, ceftazidime and piperacillin) to treat bacterial infections caused by microorganisms normally resistant to β-lactam antibiotics due to the presence of the β-lactamases.

It is to be understood that the solvents, agents, catalysts, reaction amounts, reaction temperatures, etc. described above with respect to the process and its embodiments and sub-embodiments are intended only to illustrate, not limit, the scope of the process. For example, the solvent employed in any of Steps (a) to (c) can be any organic substance which under the reaction conditions employed in the step of interest is in the liquid phase, is chemically inert, and will dissolve, suspend, and/or disperse the reactants and any reagents so as to bring the reactants and reagents into contact and to permit the reaction to proceed. Similar considerations apply to the choice of bases, catalysts, and other reagents employed in the process steps. Furthermore, each of the steps can be conducted at any temperature at which the reaction forming the desired product can detectably proceed. The reactants, catalysts and reagents in a given step can be employed in any amounts which result in the formation of at least some of the desired product. Of course, a high conversion (e.g., at least about 60% and preferably higher) of starting materials in combination with a high yield (e.g., at least about 60% and preferably higher) of desired products is typically the objective in each step, and the choice of solvents, agents, catalysts, reaction amounts, temperatures, etc. that can provide relatively good conversions and yields of product are preferred, and the choices that can provide optimal conversions and yields are more preferred. The particular solvents, agents, catalysts, reaction amounts, reaction temperatures, etc. described above with respect to the process and its embodiments and sub-embodiments can provide good to optimum conversions and yields.

The reaction times for the process steps described above depend upon such factors as (i) the choice and relative proportions of the starting substrate and other reagents, (ii) the choice of solvent, (iii) the choice of reaction temperature, and (iv) the level of conversion desired. The reactions are typically conducted for a time sufficient to achieve 100% or near 100% conversion (e.g., 99.5%, 99.0%, 98.0%, 97.0% or 95%).

The progress of any reaction step set forth herein can be followed by monitoring the disappearance of a reactant and/or the appearance of the desired product using such analytical techniques as TLC, HPLC, IR, NMR or GC.

The present invention also relates to a compound of Formula:

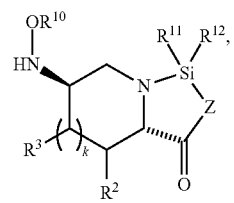

(III)

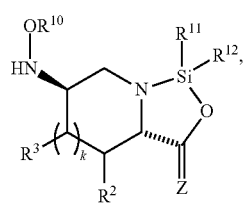

(IV)

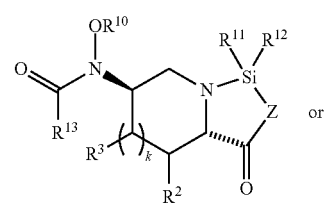

(V)

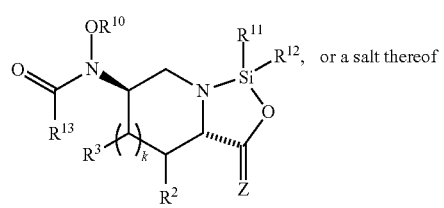

(VI)

wherein:

Z is O or —$NR^5$;

k is an integer equal to 0, 1, or 2;

$R^2$ and $R^3$ are defined as follows:

(a) $R^2$ is H, $C_{1-6}$ alkyl, —O—$C_{1-6}$ alkyl, —O—Si—$(C_{1-6}$ alkyl$)_3$, or —O—Si—$(C_{1-6}$ alkyl)(phenyl)$_2$, and each $R^3$ is H or $C_{1-6}$ alkyl; or (b) alternatively and with the proviso that k is 1 or 2, $R^2$ and the $R^3$ adjacent to $R^2$ together with the carbon atoms to which each is attached form $C_{5-7}$ cycloalkyl which is optionally substituted with from 1 to 3 substituents each of which is independently $C_{1-6}$ alkyl, —O—$C_{1-6}$ alkyl, —O—Si—$(C_{1-6}$ alkyl$)_3$, or —O—Si—$(C_{1-6}$ alkyl)(phenyl)$_2$; and any other $R^3$ is H or $C_{1-6}$ alkyl;

$R^5$ is H, $C_{1-6}$ alkyl, $C_{3-6}$ cycloalkyl, aryl, $C_{1-6}$ alkyl-aryl, heteroaryl, $C_{1-6}$ alkyl-heteroaryl, or

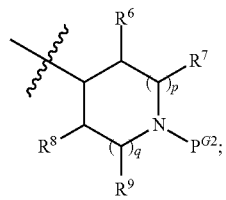

$R^6$ and $R^8$ are independently H, $C_{1-3}$ alkyl, —O—$C_{1-3}$ alkyl, or —N—$(C_{1-3}$ alkyl$)_2$;

each $R^7$ and $R^9$ is independently H or $C_{1-6}$ alkyl;

$P^{G2}$ is an amine protecting group selected from carbamates, benzylamines, sufonylamide and amides;

$R^{10}$ is benzyl or allyl, wherein the benzyl or allyl is optionally substituted with $C_{1-6}$ alkyl, $C_{1-6}$ alkoxy, fluoro, or —$NO_2$;

$R^{11}$ and $R^{12}$ are $C_{1-6}$ alkyl or aryl; or $R^{11}$ and $R^{12}$ together with the silane to which they are attached form a 4-to 6-membered saturated monocyclic ring containing 0 or 1 heteroatoms selected from N and O, which is optionally fused with 1 or 2 aromatic rings each optionally containing 0 or 1 heteroatoms selected from N and O;

$R^{13}$ is a leaving group;

p is 0, 1, or 2;

q is 0, 1, or 2;

p+q=0, 1, 2, or 3; and $R^a$ and $R^b$ are halo.

In one embodiment of the invention, Z is —$NR^5$. In one embodiment of the invention, k is 1. In one embodiment of the invention, $R^2$ and $R^3$ are H. In one embodiment of the invention, $R^5$ is H or

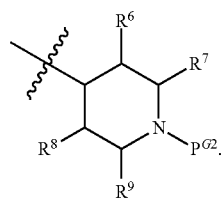

In one aspect of this embodiment, $R^5$ is

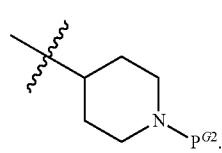

In one embodiment of the invention, $P^{G2}$ is t-Boc.

The present invention further relates to compounds including:

Exemplary Scheme

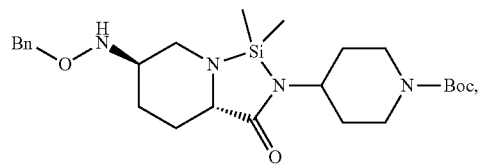

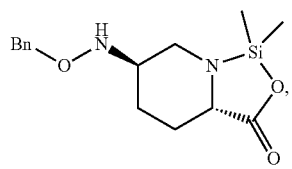

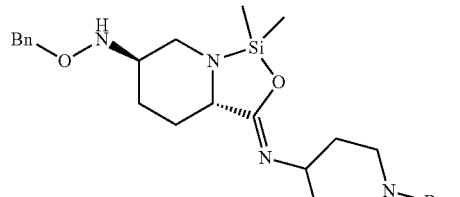

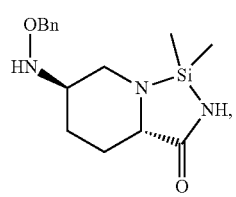 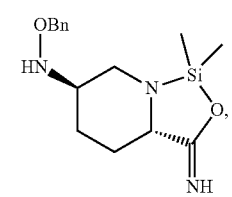

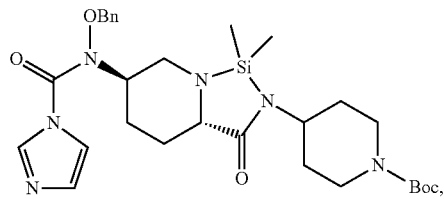

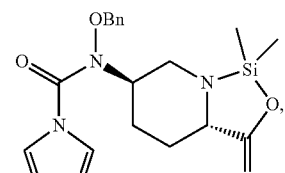

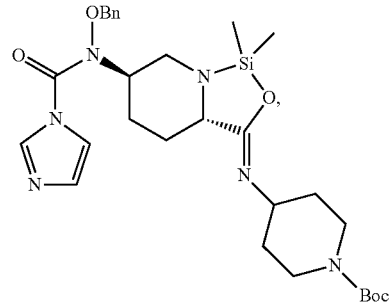

19
-continued
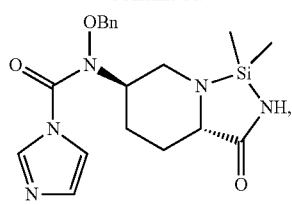
20
-continued
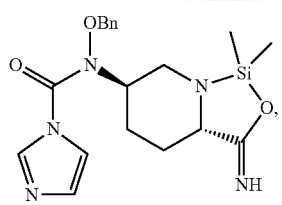
or a salt thereof.
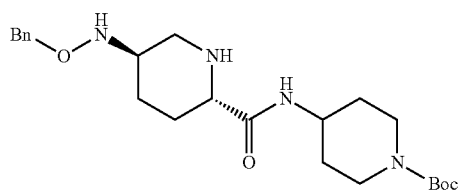
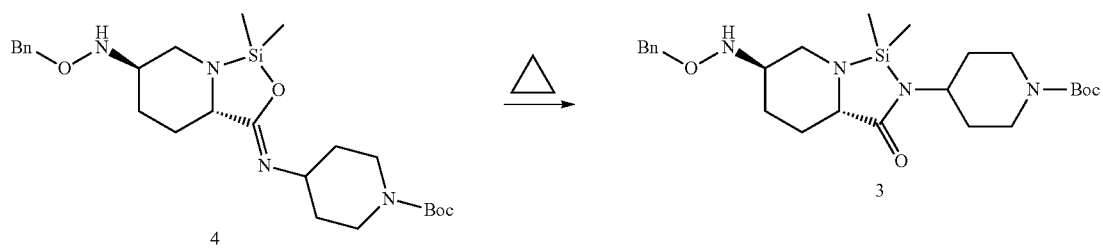
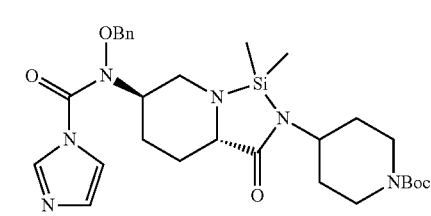

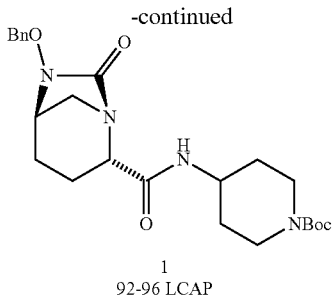

1
92-96 LCAP

Abbreviations employed herein include the following:

| | |
|---|---|
| BLI | beta-lactamase inhibitor |
| Bn | benzyl |
| Boc | t-butyloxycarbonyl |
| Cbz | carbobenzoxy (alternatively, benzyloxycarbonyl) |
| CDI | carbonyldiimidazole |
| DCM | dichloromethane |
| DIPEA | diisopropylethylamine (or Hunig's base) |
| DMAC or DMAc | N,N-dimethylacetamide |
| DME | 1,2-dimethoxyethane |
| DMF | N,N-dimethylformamide |
| Et | ethyl |
| EtOAc | ethyl acetate |
| GC | gas chromatography |
| HPLC | high-performance liquid chromatography |
| IPA | isopropyl alcohol |
| IPAc | isopropyl acetate |
| IR | infrared |
| LCAP | liquid chromatogram area percent |
| Me | methyl |
| MeCN | acetonitrile |
| MeOH | methanol |
| MTBE | methyl tert-butyl ether |
| 4-NMM | 4-methylmorpholine |
| NMP | N-methyl pyrrolidinone |
| NMR | nuclear magnetic resonance |
| pG | protective group |
| RB | round bottom |
| t-Bu | tert-butyl |
| TEA | triethylamine |
| TFA | trifluoroacetic acid |
| THF | tetrahydrofuran |
| TLC | thin layer chromatography |

The following examples serve only to illustrate the invention and its practice. The examples are not to be construed as limitations on the scope or spirit of the invention.

EXAMPLES

Example 1

Preparation of tert-butyl 4-((1R,2S,5R)-6-(benzyloxy)-7-oxo-1,6-diazabicyclo[3.2.1]octane-2-carboxamido)piperidine-1-carboxylate

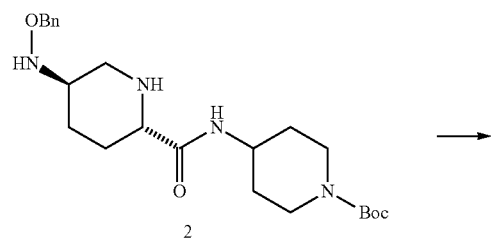

2

Diamine 2 was prepared according to Miller et al., 2014, Org. Lett. 16:174-177. In a 3 neck 100 ml RB flask with an overhead stirrer and a thermometer, diamine 2 (5 g) was slurried into acetonitrile (25 ml), followed by addition of Hunig's base (4.5 g). Dichlorodimethylsilane (2.0 g) was slowly added into the reaction mixture by controlling the temperature below 10° C. with agitation. After the addition, the mixture was agitated at this temperature for 1 hr (confirmed the full conversion to intermediate 3 or 4 by NMR).

2: $^1$H NMR (CD$_3$CN, 600 MHz): δ 1.19 (m, 1H), 1.25-1.38 (m, 3H), 1.42 (s, 9H), 1.75 (brd, 2H, J=12.9 Hz), 1.86 (m, 1H), 1.91 (m, 1H), 2.32 (dd, 1H, J=11.9, 9.8 Hz), 2.84 (m, 3H), 2.98 (dd, 1H, J=10.9, 3.1 Hz), 3.20 (m, 1H), 3.77 (m, 1H), 3.92 (brd, 2H, J=13.0 Hz), 4.62 (t, 2H, J=12.0 Hz), 5.73 (brs, 1H), 6.72 (brd, 1H, J=8.0 Hz), 7.27-7.37 (m, 5H).

3: $^1$H NMR (CD$_3$CN, 600 MHz): δ 0.26 (s, 3H), 0.29 (s, 3H), 1.06-1.18 (m, 2H), 1.37 (m, 2H), 1.41 (s, 9H), 1.76 (m, 2H), 1.87 (m, 1H), 1.97 (m, 1H), 2.36 (dd, 1H, J=12.6, 10.1 Hz), 2.63-2.78 (m, 3H), 3.17 (dd, 1H, J=11.2, 3.2 Hz), 3.36 (ddd, 1H, J=12.6, 4.4, 1.9 Hz), 3.81 (tt, 1H, J=12.1, 3.9 Hz), 4.06 (brd, 2H, J=11.6 Hz), 4.59 (d, 1H, J=11.8 Hz), 4.61 (d, 1H, J=11.8 Hz), 5.81 (d, 1H, J=6.2 Hz), 6.72 (brd, 1H, J=8.0 Hz), 7.26-7.35 (m, 5H).

4: $^1$H NMR (CD$_3$CN, 600 MHz): δ 0.21 (s, 3H), 0.25 (s, 3H), 1.17 (m, 2H), 1.29 (m, 2H), 1.40 (s, 9H), 1.58 (m, 2H), 1.85 (m, 1H), 1.93 (m, 1H), 2.42 (dd, 1H, J=12.6, 10.1 Hz), 2.45 (m, 1H), 2.71 (m, 1H), 3.31 (m, 1H), 3.43 (brd, 1H, J=10.3 Hz), 3.71 (m, 1H), 3.82 (m, 2H), 4.59 (d, 1H, J'11.8 Hz), 4.62 (d, 1H, J=11.8 Hz), 5.81 (d, 1H, J=6.1 Hz), 6.72 (brd, 1H, J=8.0 Hz), 7.26-7.35 (m, 5H).

Carbonyldiimidazole (CDI) (2.45 g) was charged into the reaction mixture. The mixture was heated at 45° C. till the full conversion to intermediate 5.

5: $^1$H NMR (CD$_3$CN, 600 MHz): δ 0.27 (s, 3H), 0.31 (s, 3H), 1.23 (m, 1H), 1.36 (m, 2H), 1.39 (s, 9H), 1.76 (m, 2H), 2.01 (m, 1H), 2.07-2.15 (m, 2H), 2.70 (brs, 2H), 3.03 (m, 1H), 3.29 (dd, 1H, J=11.9, 3.1 Hz), 3.38 (dd, 1H, J=12.7, 3.1 Hz), 3.80 (tt, 1H, J=12.1, 3.9 Hz), 3.88 (tt, 1H, J=11.6, 3.8

Hz), 4.05 (brd, 2H, J=10.3 Hz), 4.73 (t, 2H, J=10.5 Hz), 6.96 (dd, 1H, J=1.4, 0.8 Hz), 7.27-7.35 (m, 5H), 7.45 (t, 1H, J=1.4 Hz), 8.04 (t, 1H, J=0.8 Hz).

Isopropyl alcohol (IPA) (2.1g) was added into the reaction mixture at 45° C. and the reaction was agitated for 6-10 hr. Then the reaction was cooled down to room temperature.

Toluene (50 ml) was charged into the batch followed by addition of HC1 solution (2N, 35 ml) to wash the reaction mixture. The reaction mixture was phase cut to remove the bottom HCl solution which was back extracted with toluene (10 ml). The combined toluene solution was washed with sat. NaHCO₃ (15 ml), followed by water (10 ml) wash. The final toluene solution was concentrated down to 2.5 volumes (13 ml), followed by slow addition of heptane (70 ml) to afford a slurry. The final urea compound 1 (4.95 g, 93% yield) was isolated by filtration and washed with heptane/toluene (6:1) solution.

1: ¹H NMR (CDCl₃, 500 MHz) δ: 7.45-7.32 (m, 5 H), 6.55 (d, J =8.2 Hz, 1 H), 5.05 (d, J =11.6 Hz, 1 H), 4.90 (d, J =11.6 Hz, 1 H), 4.02 (m, 2 H), 3.90 (m, 2 H), 3.30 (m, 1 H), 2.99 (dt, J=11.7, 1.1 Hz, 1 H), 2.86 (m, 2 H), 2.64 (d, J=11.7 Hz, 1 H), 2.37 10 (dd, J=14.6, 6.9 Hz, 1 H), 2.04-1.82 (m, 4 H), 1.58 (m, 1 H), 1.45 (s, 9 H), 1.30 (m, 2H); ¹³C NMR (CDCl₃, 125 MHz) δ: 168.3, 167.5, 154.7, 135.6, 129.2 (2 C), 128.8, 128.6 (2 C), 79.7, 78.3, 60.4, 57.8, 47.5, 46.8, 42.5 (br, 2 C), 32.0, 31.7, 28.4 (3 C), 20.8, 17.2.

Example 2

Preparation of tert-butyl 4-((1R,2S,5R)-6-hydroxy-7-oxo-1,6-diazabicyclo[3.2.1]octane-2-carboxamido)piperidine-1-carboxylate Compound 1 prepared according to Example 1 was used in the subsequent hydro-debenzylation reaction shown below. Compound 1 prepared using triphosgene was used as a comparator.

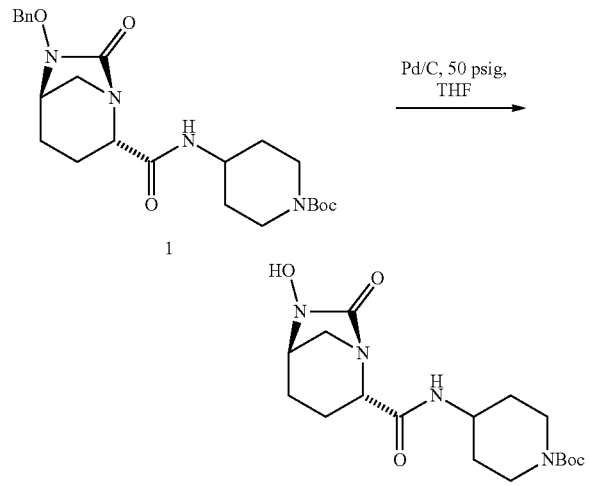

Into a dried and cleaned autoclave was charged urea 1 (3.0g) and THF (72 mL). Then Pd/C (10 wt % loading) was charged into the reaction mixture, followed by charging H₂ to 50 psig (total inside pressure). The mixture was aged at 25° C., 50 psig for 4 hours to achieve a full conversion. The reaction mixture was vented with H₂ gas and filtered to remove Pd/C and washed with THF (5× vol., 15 mL). The organic solution was concentrated down to ⅒ volume and the solvent switched to IPAc (45 ml) to afford a slurry of the product. The slurry was agitated for an additional 4 hr. The reaction mixture was filtered to collect the solid and washed with IPAc (9 mL) to afford a white solid. The solid was dried under vacuum and N₂ sweep to afford the title compound (~95% yield, >98 LCAP). Spectral data matched that of the previously reported compound. See Mangion et al., 2011, Org. Lett. 13:5480. Table 1 shows the comparison of urea 1 prepared using the process of the invention (i.e., with a silicon-containing compound and CDI) or a previously published process (i.e., with triphosgene) in the subsequent hydroxyl-debenzylation reaction.

TABLE 1

|  | Conversion (%) | Reaction time (hr) |
|---|---|---|
| Urea made by triphosgene | 50 | 18 |
| Urea made by CDI | 100 | 2 |

While the foregoing specification teaches the principles of the present invention, with examples provided for the purpose of illustration, the practice of the invention encompasses all of the usual variations, adaptations and/or modifications that come within the scope of the following claims.

What is claimed is:

1. A process for preparing a compound of Formula I:

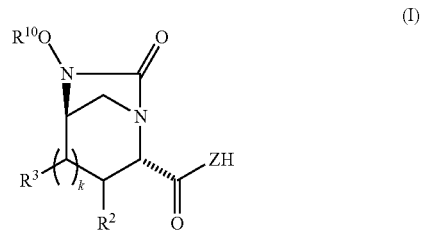

or a pharmaceutically acceptable salt thereof; comprising:

(a) reacting a compound of Formula (II):

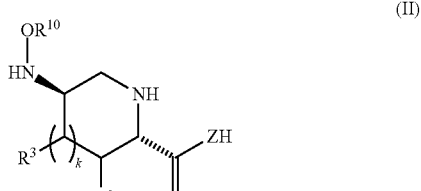

with a compound of formula (X)

and a base to obtain a compound of Formula (III) or (IV), or a mixture thereof;

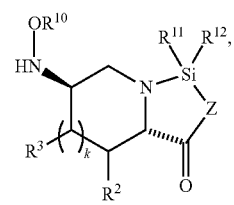

(III)

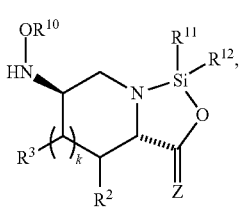

(IV)

(b) treating the compound of formula (III) or (IV), or the mixture thereof, with phosgene or a phosgene equivalent to obtain a compound of formula (V) or (VI), or a mixture thereof

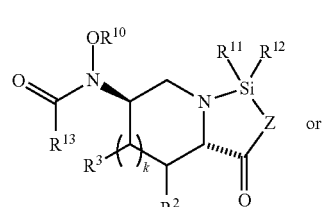

(V)

or

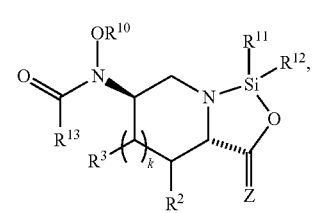

(VI)

and (c) treating the compound of formula (V) or (VI), or a mixture thererof, with a hydrolysis reagent to obtain the compound of formula (I);

wherein

Z is O or $-NR^5$;

k is an integer equal to 0, 1, or 2;

$R^2$ and $R^3$ are defined as follows:

(a) $R^2$ is H, $C_{1-6}$ alkyl, $-O-C_{1-6}$ alkyl, $-O-Si-(C_{1-6}$ alkyl)$_3$, or $-O-Si-(C_{1-6}$ alkyl)(phenyl)$_2$, and each $R^3$ is H or $C_{1-6}$ alkyl; or (b) alternatively and with the proviso that k is 1 or 2, $R^2$ and the $R^3$ adjacent to $R^2$ together with the carbon atoms to which each is attached form $C_{5-7}$ cycloalkyl which is optionally substituted with from 1 to 3 substituents each of which is independently $C_{1-6}$ alkyl, $-O-C_{1-6}$ alkyl, $-O-Si-(C_{1-6}$ alkyl)$_3$, or $-O-Si-(C_{1-6}$ alkyl)(phenyl)$_2$; and any other $R^3$ is H or $C_{1-6}$ alkyl;

$R^5$ is H, $C_{1-6}$ alkyl, $C_{3-6}$cycloalkyl, aryl, $-C_{1-6}$alkyl-aryl, heteroaryl, $-C_{1-6}$alkyl-heteroaryl, or

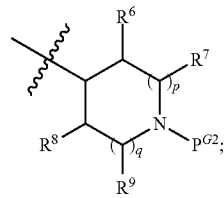

$R^6$ and $R^8$ are independently H, $C_{1-3}$ alkyl, $-O-C_{1-3}$ alkyl, or $-N-(C_{1-3}$ alkyl)$_2$;

each $R^7$ and $R^9$ is independently H or $C_{1-6}$ alkyl;

$P^{G2}$ is an amine protecting group selected from carbamates, benzylamines, sulfonamides and amides;

$R^{10}$ is benzyl or allyl, wherein the benzyl or allyl is optionally substituted with $C_{1-6}$ alkyl, $C_{1-6}$ alkoxy, fluoro, or $-NO_2$;

$R^{11}$ and $R^{12}$ are $C_{1-6}$ alkyl or aryl; or $R^{11}$ and $R^{12}$ together with the silane to which they are attached form a 4-to 6-membered saturated monocyclic ring containing 0 or 1 heteroatoms selected from N and O, which is optionally fused with 1 or 2 aromatic rings each optionally containing 0 or 1 heteroatoms selected from N and O;

$R^{13}$ is a leaving group;

p is 0, 1, or 2;

q is 0, 1, or 2;

p+q=0, 1, 2, or 3; and $R^a$ and $R^b$ are halo.

2. The process of claim 1, wherein Z is $-NR^5$.
3. The process of claim 1, wherein k is 1.
4. The process of claim 1, wherein $R^2$ and $R^3$ are H.
5. The process of claim 1, wherein $R^5$ is H or

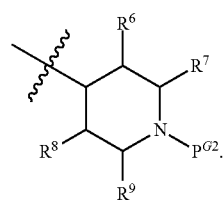

6. The process of claim 4, wherein $R^5$ is

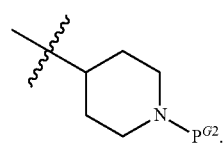

7. The process of claim 1, wherein $P^{G2}$ is t-Boc.
8. The process of claim 1, wherein the compound of Formula X is a dihalodialkylsilane, dihalodiarylsilane, or dihaloalkylarylsilane.

9. The process of claim 8, wherein the compound of Formula X is dichlorodimethylsilane.

10. The process of claim 1, wherein the base is Hunig's base.

11. The process of claim 1, wherein the phosgene equivalent is carbonyldiimidazole.

12. The process of claim 1, wherein the hydrolysis reagent is a protic solvent, acid, or fluoride source.

13. The process of claim 12, wherein the hydrolysis reagent is a protic solvent.

14. The process of claim 13, wherein the protic solvent is isopropyl alcohol.

15. The process of claim 1, wherein the compound of Formula (I) is tert-butyl 4-((2S,5R)-7-oxo-6-benzyloxy-1,6-diazabicyclo[3.2.1]octane-2-carboxamido)piperidine-1-carboxylate or a pharmaceutically acceptable salt thereof.

16. A compound which is:

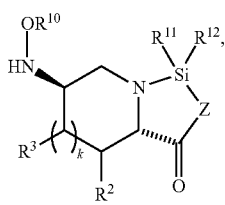
(III)

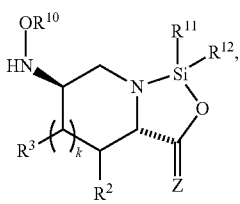
(IV)

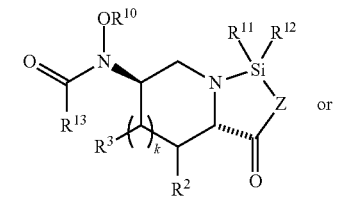
(V) or

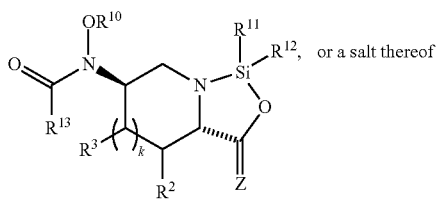
(VI) or a salt thereof wherein
Z is O or —NR$^5$;
k is an integer equal to 0, 1, or 2;
R$^2$ and R$^3$ are defined as follows:
(a) R$^2$ is H, C$_{1-6}$ alkyl, —O—C$_{1-6}$ alkyl, —O—Si—(C$_{1-6}$ alkyl)$_3$, or —O—Si—(C$_{1-6}$ alkyl)(phenyl)$_2$, and each R$^3$ is H or C$_{1-6}$ alkyl; or
(b) alternatively and with the proviso that k is 1 or 2, R$^2$ and the R$^3$ adjacent to R$^2$ together with the carbon atoms to which each is attached form C$_{5-7}$ cycloalkyl which is optionally substituted with from 1 to 3 substituents each of which is independently C$_{1-6}$ alkyl, —O—C$_{1-6}$ alkyl, —O—Si—(C$_{1-6}$ alkyl)$_3$, or —O—Si—(C$_{1-6}$ alkyl)(phenyl)$_2$; and any other R$^3$ is H or C$_{1-6}$ alkyl;

R$^5$ is H, C$_{1-6}$ alkyl, C$_{3-6}$ cycloalkyl, aryl, C$_{1-6}$ alkyl-aryl, heteroaryl, C$_{1-6}$ alkyl-heteroaryl, or

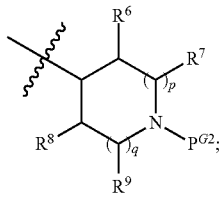

R$^6$ and R$^8$ are independently H, C$_{1-3}$ alkyl, —O—C$_{1-3}$ alkyl, or —N—(C$_{1-3}$ alkyl)$_2$;

each R$^7$ and R$^9$ is independently H or C$_{1-6}$ alkyl;

P$^{G2}$ is an amine protecting group selected from carbamates, benzylamines, sulfonamides, and amides;

R$^{10}$ is benzyl or allyl, wherein the benzyl or allyl is optionally substituted with C$_{1-6}$ alkyl, C$_{1-6}$ alkoxy, fluoro, or —NO$_2$;

R$^{11}$ and R$^{12}$ are C$_{1-6}$ alkyl or aryl; or

R$^{11}$ and R$^{12}$ together with the silane to which they are attached form a 4-to 6-membered saturated monocyclic ring containing 0 or 1 heteroatoms selected from N and O which is optionally fused with 1 or 2 aromatic rings each optionally containing 0 or 1 heteroatoms selected from N and O;

R$^{13}$ is a leaving group;

p is 0, 1, or 2;

q is 0, 1, or 2;

p+q=0, 1, 2, or 3.

17. The compound of claim 16, wherein Z is —NR$^5$.

18. The compound of claim 16 which is:

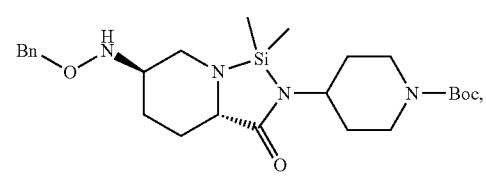

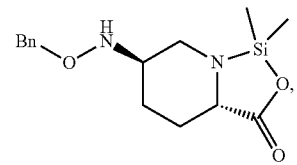

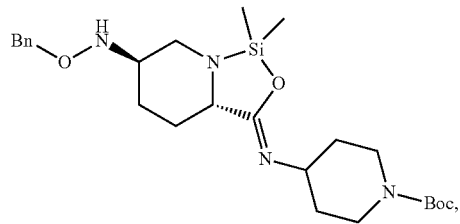

-continued
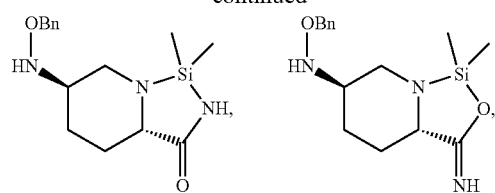
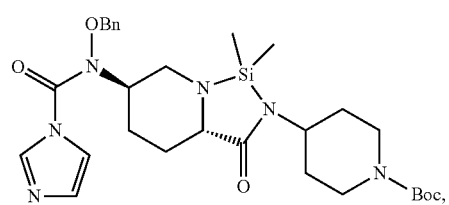
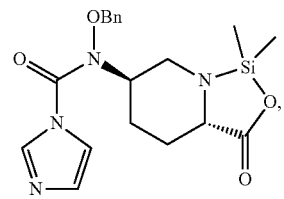
-continued
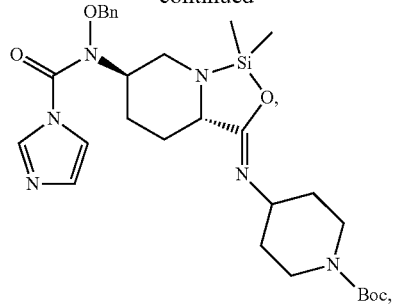
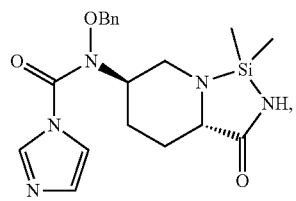
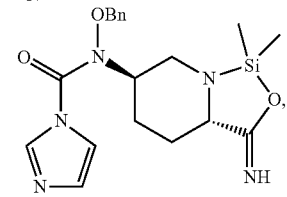
or a salt thereof.
* * * * *